(12) United States Patent
Zeng et al.

(10) Patent No.: US 12,059,175 B2
(45) Date of Patent: Aug. 13, 2024

(54) DEVICE FOR ADJUSTING BIOPSY ANGLES AND BIOPSY NEEDLE GUIDE

(71) Applicant: JingFang Precision Medical Device (Shenzhen) Co., Ltd., Guangdong (CN)

(72) Inventors: Weihua Zeng, Guangdong (CN); Junhua Zeng, Guangdong (CN); Jianfeng Zou, Guangdong (CN)

(73) Assignee: JingFang Precision Medical Device (Shenzhen) Co., Ltd., Shenzhen (CN)

( * ) Notice: Subject to any disclaimer, the term of this patent is extended or adjusted under 35 U.S.C. 154(b) by 225 days.

(21) Appl. No.: 17/786,049

(22) PCT Filed: Jan. 3, 2020

(86) PCT No.: PCT/CN2020/070307
§ 371 (c)(1),
(2) Date: Jun. 16, 2022

(87) PCT Pub. No.: WO2021/128449
PCT Pub. Date: Jul. 1, 2021

(65) Prior Publication Data
US 2023/0022542 A1    Jan. 26, 2023

(30) Foreign Application Priority Data

Dec. 27, 2019   (CN) .......................... 201911400419.5
Dec. 27, 2019   (CN) .......................... 201922446624.7

(51) Int. Cl.
*A61B 17/34*   (2006.01)
(52) U.S. Cl.
CPC .. *A61B 17/3403* (2013.01); *A61B 2017/3405* (2013.01); *A61B 2017/3413* (2013.01)

(58) Field of Classification Search
None
See application file for complete search history.

(56) References Cited

U.S. PATENT DOCUMENTS

2019/0282263 A1* 9/2019 Kincaid ................. A61B 90/11

FOREIGN PATENT DOCUMENTS

| CN | 101756715 A | 6/2010 |
|----|-------------|--------|
| CN | 103263295 B | 12/2014 |

(Continued)

OTHER PUBLICATIONS

CN-207506622-U translation (Year: 2018).*

(Continued)

*Primary Examiner* — Jason M Ip
*Assistant Examiner* — Renee C Langhals (57) ABSTRACT

A device for adjusting biopsy angles and a biopsy needle guide are provided. The device for adjusting biopsy angles comprises an angle fixing base and a needle guiding base, the needle guiding base being rotatably connected with the angle fixing base at their first ends, the needle guiding base having a needle tract for guiding a biopsy needle, wherein an U-shaped limiting assembly formed on one side of the needle guiding base surrounds a angle fixing sheet extending from the angle fixing base at their second ends, and a positioning adjuster mounted on the U-shaped limiting assembly is movably engaged with positioning holes on the angle fixing sheet so as to be inserted into the positioning holes or be released out of the positioning holes. The needle guiding base can be rotated at a large angle to disengage from the angle fixing sheet, and is convenient for cleaning.

12 Claims, 6 Drawing Sheets

(56) References Cited

FOREIGN PATENT DOCUMENTS

| CN | 105708527 | A | * | 6/2016 | ......... | A61B 17/3403 |
| CN | 107280739 | A | * | 10/2017 | ......... | A61B 17/3401 |
| CN | 207506622 | U | * | 6/2018 | | |
| CN | 207506622 | U | | 6/2018 | | |
| CN | 207561960 | U | * | 7/2018 | | |
| CN | 207561960 | U | | 7/2018 | | |

OTHER PUBLICATIONS

CN-207561960-U translation (Year: 2018).*
CN-107280739-A translation (Year: 2017).*
CN-105708527-A translation (Year: 2016).*
International Search Report of PCT Patent Application No. PCT/CN2020/070307 issued on Aug. 28, 2020.

* cited by examiner

DEVICE FOR ADJUSTING BIOPSY ANGLES AND BIOPSY NEEDLE GUIDE

FIELD

The present application generally relates to ultrasound interventional medical instruments, more particularly to a device for adjusting biopsy angles and a biopsy needle guide using the same device.

BACKGROUND

At present, when using external ultrasound probes for interventional diagnosis and treatment, doctors will choose different needle insertion angles to perform biopsy operations according to depth of biopsy targets. Commonly used needle guiding brackets are basically multi-angle adjustable and optional. For example, in a Chinese invention patent with issued no. CN103263295B, titled "Angle Adjusting Device for Biopsy Needle Guide and Biopsy Needle Guide", an angle adjusting device is disclosed, wherein an arc-shaped adjusting groove is formed on a adjusting plate and different gear steps are formed on the outer side of the arc-shaped adjusting groove, and a connecting rod traverses the arc-shaped adjusting groove, with one end being fixedly connected with a needle guide, the other end being connected with a fastening assembly. When the connecting rod moves back and forth within a range defined by the arc-shaped adjusting groove under the action of external force, the connecting rod drives the needle guide to rotate around a pin shaft within an angle range defined by the arc-shaped adjusting groove. Angle adjustment and positioning operations of the biopsy needle guide are simple and fast, but the rotation angle range of the needle guide is limited by the arc-shaped adjusting groove, and the needle guide cannot be completely disengaged from the adjusting plate, thus the biopsy needle guide is inconvenient to clean and easy to hide dirt.

SUMMARY

The technical problem to be solved by the present application is to provide a device for adjusting biopsy angles that can be rotated and separated for easy cleaning and a biopsy needle guide using the same device, in view of the above-mentioned drawbacks of the prior art.

In order to solve the technical problem, in a first aspect the present application provides a device for adjusting biopsy angles, comprising an angle fixing base and a needle guiding base, the needle guiding base being rotatably connected with the angle fixing base at their first ends, and the needle guiding base having a needle tract for guiding a biopsy needle, wherein an angle fixing sheet extends from a second end of the angle fixing base, and two or more positioning holes are distributed on the angle fixing sheet with a certain radius around a rotation axis at the first ends of the needle guiding base and the angle fixing base; a U-shaped limiting assembly is formed at a second end of the needle guiding base on the side opposite to the angle fixing sheet, the U-shaped limiting assembly surrounds the angle fixing sheet therein, and at least an inner side surface of the angle fixing sheet is in contact with an inner side limiting surface of the U-shaped fixing assembly; and the device for adjusting biopsy angles further comprises a positioning adjuster mounted on the U-shaped limiting assembly, and the positioning adjuster is movably engaged with the positioning holes on the angle fixing sheet so as to be inserted into the positioning holes or be released out of the positioning holes.

In the device for adjusting biopsy angles according to an embodiment of the present application, the U-shaped limiting assembly is formed by an enclosure of a first limiting plate extending laterally from one side of the second end of the needle guiding base, a second limiting plate extending vertically from the first limiting plate and the needle guiding base, and an outer side surface of the needle guiding base and an inner side surface of the second limiting plate serve as the inner side limiting surface and an outer side limiting surface of the U-shaped limiting assembly respectively.

In the device for adjusting biopsy angles according to an embodiment of the present application, the positioning adjuster comprises a positioning post which movably penetrates through the second limiting plate and cooperates with the positioning holes.

In the device for adjusting biopsy angles according to an embodiment of the present application, the positioning post penetrates through the second limiting plate by means of elastically loaded shaft-hole cooperation or threaded rotation, and the positioning post has an operating portion at its outer end.

In the device for adjusting biopsy angles according to an embodiment of the present application, the positioning hole is formed with a tapered groove, and a tapered platform corresponding to the tapered groove is provided at an inner end of the positioning post.

In the device for adjusting biopsy angles according to an embodiment of the present application, a retaining ring is provided at an inner end of the positioning post passing through the second limiting plate, and when the retaining ring abuts against the inner side surfaces of the second limiting plate, the positioning post is prevented from being disengaged from the second limiting plate.

In the device for adjusting biopsy angles according to an embodiment of the present application, opening slots corresponding to and penetrating to each of the positioning holes are formed on an outer edge of the angle fixing sheet.

In the device for adjusting biopsy angles according to an embodiment of the present application, the needle guiding base is rotatably connected with the angle fixing base at their first ends through a rotating shaft.

In the device for adjusting biopsy angles according to an embodiment of the present application, the needle guiding base further comprises: a first guiding seat, the first guiding seat having a needle guiding channel penetrating from the first end to the second end and at least one groove traversing the needle guiding channel provided from the first end to the second end corresponding to the needle guiding channel; a second guiding seat, the second guiding seat having a matching surface that cooperates with the needle guiding channel and engaging members that extends respectively from two sides on the matching surface at a position corresponding to the groove; and the second guiding seat is rotatably mounted on the first guiding seat by means of elastic loading configuration, and elastic force of the elastic loading configuration causes the matching surface on the second guiding seat to have a tendency to move close to the needle guiding channel of the first guiding seat, so that the matching surface and the needle guiding channel together form the needle tract; and the elastic force of the elastic loading configuration also causes the engaging members on the second guiding seat to have a tendency to move into the corresponding groove on the first guiding seat, so that the engaging members are positioned in the corresponding groove; wherein the first end of the first guiding seat is rotatably connected with the angle fixing base, and the U-shaped limiting assembly is formed at the second end of the first guiding seat.

In order to solve the technical problem, in a second aspect the present application provides a biopsy needle guide, comprising a mounting assembly used for cooperating with an ultrasound probe, and further comprising the device for adjusting biopsy angles, and the angle fixing base of the device for adjusting biopsy angles is arranged on the mounting assembly.

Implementing the device for adjusting biopsy angles and the biopsy needle guide using the same device of the present application has the following beneficial effects: in the device for adjusting biopsy angles according to embodiments of the present application, the needle guiding base is rotatably connected with the angle fixing base at their first ends, and U-shaped limiting assembly formed on one side of the needle guiding base surrounds the angle fixing sheet extending from the angle fixing base at their second ends, and the positioning adjuster mounted on the U-shaped limiting assembly can movably cooperate with the positioning holes on the angle fixing sheet to determine the biopsy angles, and when the positioning adjuster is completely disengaged from a positioning hole, the needle guiding base can be rotated along the angle fixing sheet to determine an angle gear, and can also be rotated at a large angle to completely disengage from the angle fixing sheet, forming enough cleaning space and solving the problem of being difficult to clean the biopsy needle guide.

BRIEF DESCRIPTION OF THE DRAWINGS

The present application will be further described with reference to the accompanying drawings and embodiments, in which.

DETAILED DESCRIPTION

To explain objects, technical solutions and advantages of the present application more clearly, the present application will be further described with reference to the accompanying drawings and embodiments in the following. It should be understood that, the specific embodiments described here are only for explanation, but not for limitation to the present application. Also, the embodiments and technical features in the embodiments of the present application may be combined with each other without conflict.

Figure 1:
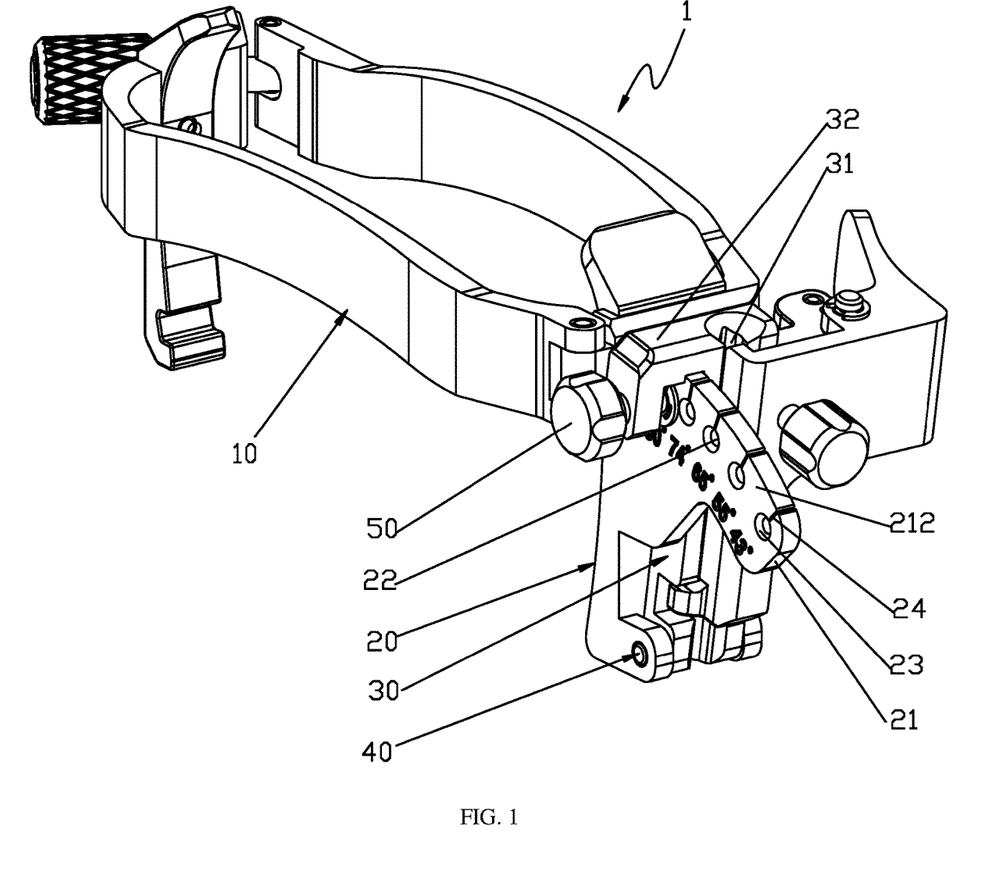
FIG. 1 is a schematic structural diagram of a biopsy needle guide according to an embodiment of the present application.
Figure 2:
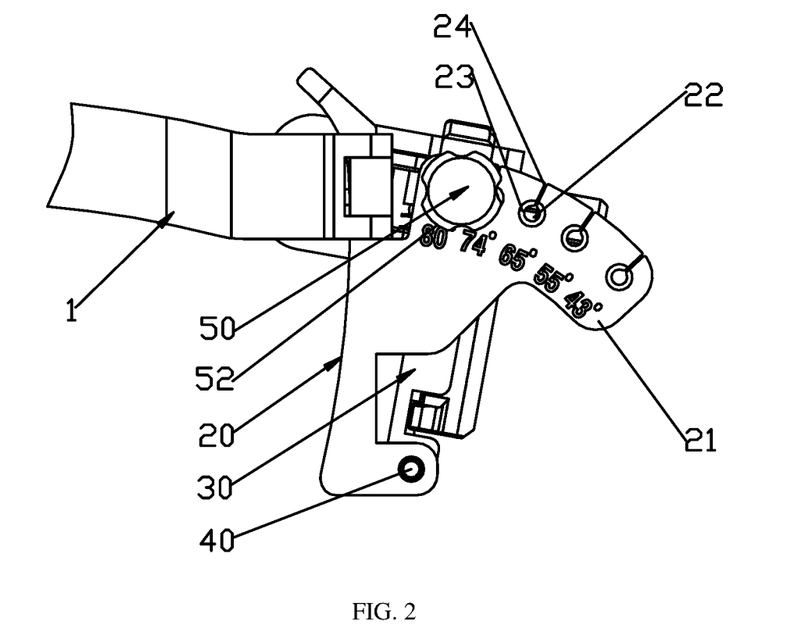
FIG. 2 is a partial structural plan view of the biopsy needle guide as shown in FIG. 1.
Figure 5:
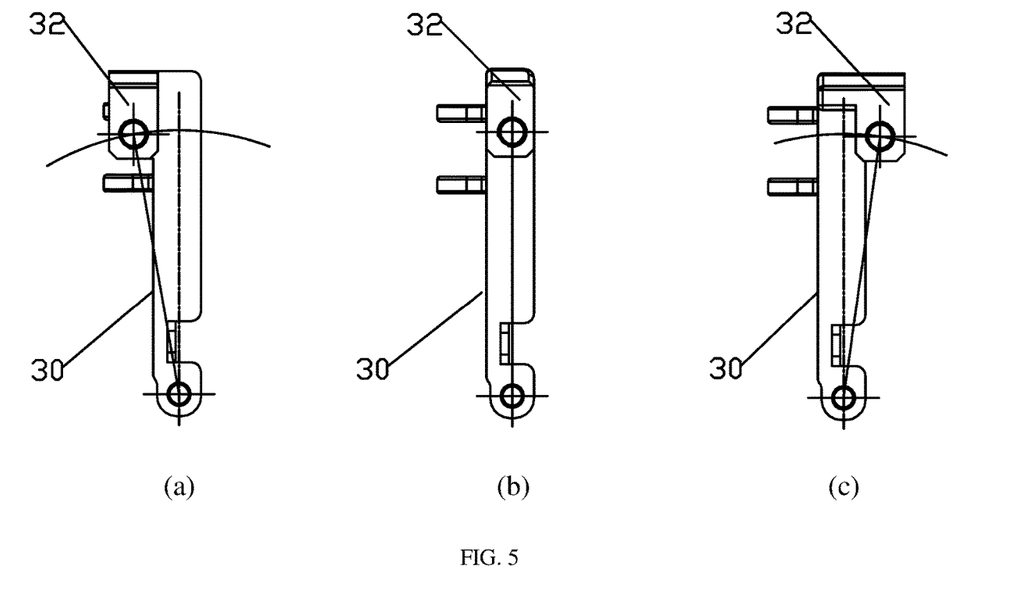
FIG. 5 is a schematic diagram showing different setting states of a U-shaped limiting assembly relative to a needle tract according to an embodiment of the present application.
Figure 6:
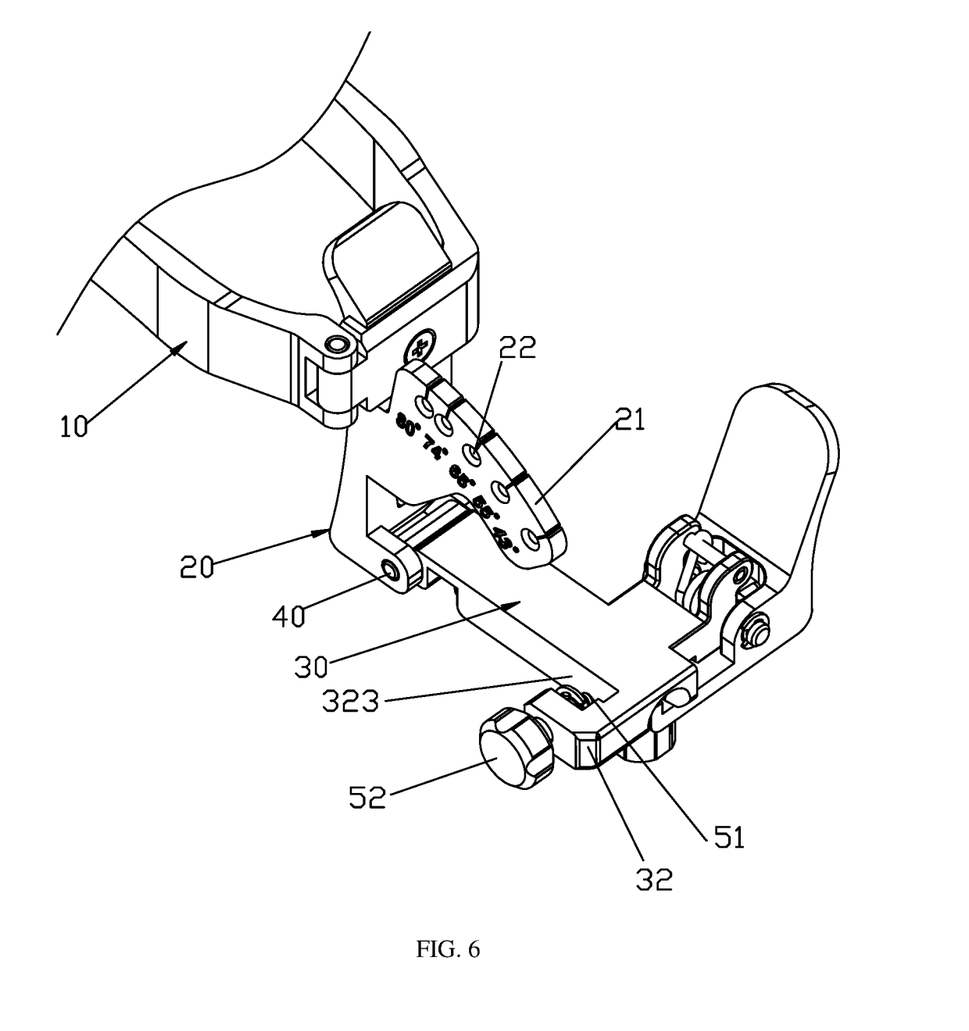
FIG. 6 is a structural schematic diagram of the device for adjusting biopsy angles in the biopsy needle guide as shown in FIG. 1 with a needle guiding base being rotated and opened at a large angle.

As shown in FIG. 1 and FIG. 2, a biopsy needle guide 1 according to an embodiment of the present application comprises a mounting assembly 10 and a device for adjusting biopsy angles provided on the mounting assembly 10. The mounting assembly 10 is used for cooperating with an ultrasound probe. The device for adjusting biopsy angles further comprises an angle fixing base 20 and a needle guiding base 30, the angle fixing base 20 is arranged on the mounting assembly 10, and the needle guiding base 30 has a needle tract 31 for guiding a biopsy needle to achieve interventional operation. The needle guiding base 30 is rotatably connected with the angle fixing base 20 at their first ends through a rotating shaft 40. An angle fixing sheet 21 extends from a second end of the angle fixing base 20, and two or more positioning holes 22 are distributed on the angle fixing sheet 21 with a certain radius around an axis of the rotating shaft 40. A U-shaped limiting assembly 32 is formed at a second end of the needle guiding base 30 on the side opposite to the angle fixing sheet 21. The U-shaped limiting assembly 32 surrounds the angle fixing sheet 21 therein to form a three-sided enclosure to the angle fixing sheet 21, but the rotation of the U-shaped limiting assembly 32 relative to the angle fixing sheet 21 is not restricted. Referring specifically to FIG. 5, the U-shaped limiting assembly 32 can extend parallel to the needle tract 31 on the needle guiding base 30, as shown in figure (b) of FIG. 5; the U-shaped limiting assembly 32 can also extend clockwise along the rotation direction, that is, the U-shaped limiting assembly 32 is relatively located in front of the needle guiding base 30 in a clockwise rotation direction, as shown in figure (c) of FIG. 5; or, the U-shaped limiting assembly 32 can extend counterclockwise along the rotation direction, that is, the U-shaped limiting assembly 32 is relatively located behind the needle guiding base 30 in a counterclockwise rotation direction, as shown in figure (a) of FIG. 5. A positioning adjuster 50 is also mounted on the U-shaped limiting assembly 32, and the positioning adjuster 50 is movably engaged with the positioning holes 22 on the angle fixing sheet 21. When the positioning adjuster 50 is inserted into a positioning hole 22 for positioning, a biopsy angle is locked, and the rotation of the needle guiding base 30 relative to the angle fixing base 20 is restricted. When the positioning adjuster 50 is released out of the positioning hole 22, other angle gears that need to be adjusted can be selected by rotating the needle guiding base 30 relative to the angle fixing base 20, and the U-shaped limiting assembly 32 can be completely removed from the angle fixing sheet 21 by rotating the needle guiding base 30 relative to the angle fixing base 20 at a large angle, and then enough cleaning space can be exposed to facilitate cleaning of the biopsy needle guide, as shown in FIG. 6.

Figure 3:
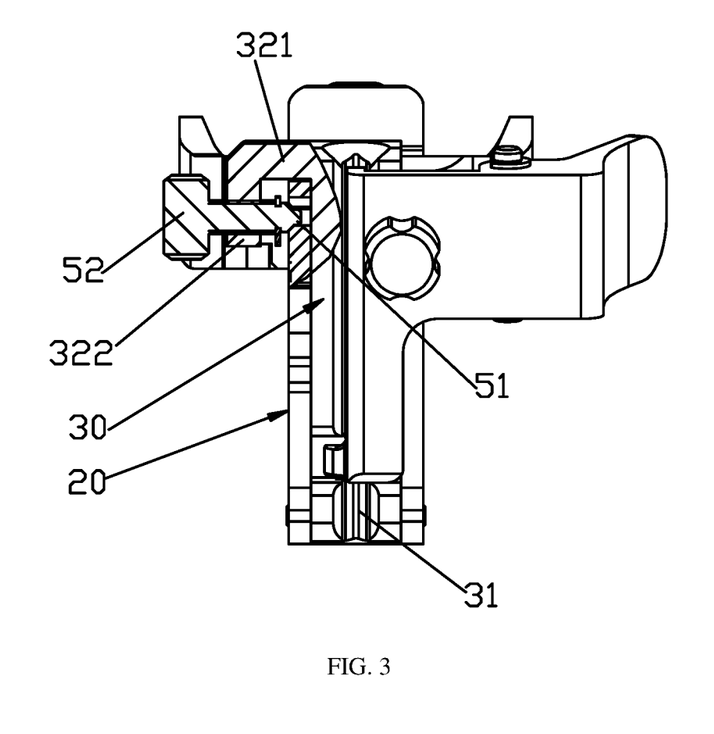
FIG. 3 is a structural cross-sectional view of a device for adjusting biopsy angles in the biopsy needle guide as shown in FIG. 1.
Figure 4:
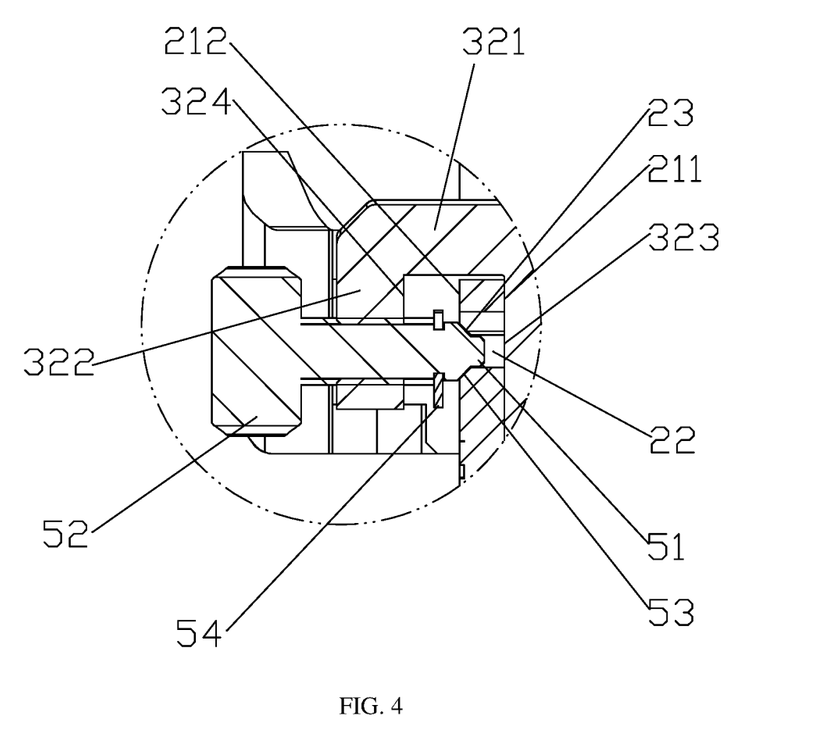
FIG. 4 is an enlarged view of partial structure as shown in FIG. 3.

Specifically, as shown in FIG. 3 and FIG. 4, the U-shaped limiting assembly 32 is formed by an enclosure of a first limiting plate 321 extending laterally from one side of the second end of the needle guiding base 30, a second limiting plate 322 extending vertically downward from the first limiting plate 321 and the needle guiding base 30, and they surrounds the angle fixing sheet 21 from above. An outer side surface 323 of the needle guiding base 30 serves as an inner side limiting surface of the U-shaped limiting assembly 32, and an inner side surface 324 of the second limiting plate 322 serves as an outer side limiting surface of the U-shaped limiting assembly 32. An inner side surface 211 of the angle fixing sheet 21 is in contact with the outer side surface 323 of the needle guiding base 30 to provide guiding effect for the rotation of the needle guiding base 30 relative to the angle fixing base 20. According to different embodiments of the present application, the U-shaped limiting assembly may further consists of a first limiting plate laterally extending from the second end of the needle guiding base near the middle to one side, a second limiting plate extending vertically upward from the first limiting plate and the needle guiding base, and they surrounds the angle fixing sheet 21 from below.

Further as shown in FIG. 3 and FIG. 4, the positioning adjuster 50 comprises a positioning post 51, which movably penetrates through the second limiting plate 322 and cooperates with the positioning holes 22 on the angle fixing sheet 21. Specifically, in the embodiment shown in FIG. 3 and FIG. 4, the positioning post 51 is threaded through the second limiting plate 322 in a way of threaded rotation, and the positioning post 51 has an operating portion 52 at its outer end. By rotating the operation portion 52, the positioning post 51 can be inserted into the positioning hole 22, and by rotating the operation portion 52 in an opposite direction, the positioning post 51 can be released from the positioning hole 22. Further as shown in FIG. 4, each positioning hole 22 is processed to form a tapered groove 23, and a tapered platform 53 corresponding to the tapered groove 23 is provided at the inner end of the positioning post 51. When the operating portion 52 is rotated, the positioning post 51 is inserted into the positioning hole 22 via threaded rotation to form a preliminary limit status, and the tapered groove 23 provides guiding function at this time; and then the operating portion 52 is continuedly rotated, and when the outer side surface 323 of the needle guiding base 30 is in contact with the inner side surface 211 of the angle fixing sheet 21, a tightened rotation of the operating portion 52 causes the tapered platform 53 to rest against the tapered groove 23, and the tapered groove 23 provides positioning and locking function at this time, so as to realize a stable and precise positioning status. When the operating portion 52 is rotated to make the positioning post 51 being released out of the positioning hole 22, the needle guiding base 30 can be rotated to adjust the biopsy angle gear and can be opened at a large angle for cleaning. In order to prevent the positioning post 51 from being completely disengaged from the second limiting plate 322, a retaining ring 54 can also be provided at the inner end of the positioning post 51 passing through the second limiting plate 322. When the retaining ring 54 abuts against the inner side surfaces 324 of the second limiting plate 322 during rotation of the positioning post 54, the positioning post 51 is prevented from being disengaged from the second limiting plate 322. Specifically, the retaining ring 54 can be an open retaining ring stuck on the positioning post 51, or a closed retaining ring welded on the positioning post 51, or can be realized by directly filling the thread with welding wire to limit the threaded rotation. Further referring to FIG. 4, in the locking and positioning configuration between the U-shaped limiting assembly 32, the angle fixing sheet 21 and the positioning adjuster 50, the inner side limiting surface of the U-shaped limiting assembly 32 (i.e., the outer side surface 323 of the needle guiding base 30) is in contact with the inner side surface 211 of the angle fixing sheet 21, while there is a certain distance between the outer side limiting surface of the U-shaped limiting assembly 32 (i.e., the inner side surface 324 of the second limiting plate 322) and the outer side surface 212 of the angle fixing sheet 21 to provide a rotary installation stroke for the positioning post 51. When the retaining ring 54 abuts against the inner side surface 324 of the second limit plate 322, an inner end surface of the positioning post 51 must have left the outer side surface 212 of the angle fixing sheet 21, thus the entire needle guiding base 30 can realize free rotation without interference and obstruction.

In the embodiment of the present application described above with reference to FIG. 3 and FIG. 4, the positioning post 51 is threaded through the second limiting plate 322 to cooperate with the positioning holes 22. It is obvious to those skilled in the art that, the positioning post 51 can also be movably penetrated through the second limiting plate 322 in other suitable manners. For example, means of elastically loaded shaft and holes such as a latch can also be used between the positioning post 51 and the second limiting plate 322 to realize gear adjustment by means of cooperation between the positioning post 51 and the positioning holes 22.

Referring to FIG. 1 and FIG. 2 again, the angle fixing sheet 21 is provided with two or more positioning holes 22 and each positioning hole 22 is machined with a tapered groove 23. With current conventional processing methods, each positioning hole 22 needs to be positioned and processed for multiple times, and this may bring a large cumulative error, which affects positioning accuracy of angle gears, thereby affecting accuracy of the biopsy operation. Therefore, in the illustrated embodiment, an opening slot 24 is formed on each positioning hole 22, and the opening slot 24 penetrates from an outer edge of the angle fixing sheet 21 to the positioning hole 22, so that the outer edge of the angle fixing sheet 21 communicates with the positioning hole 22 through the opening slot 24, and wire cutting programming can be processed in one step continuously, thus the machining precision is high and the positioning is accurate.

Figure 7:
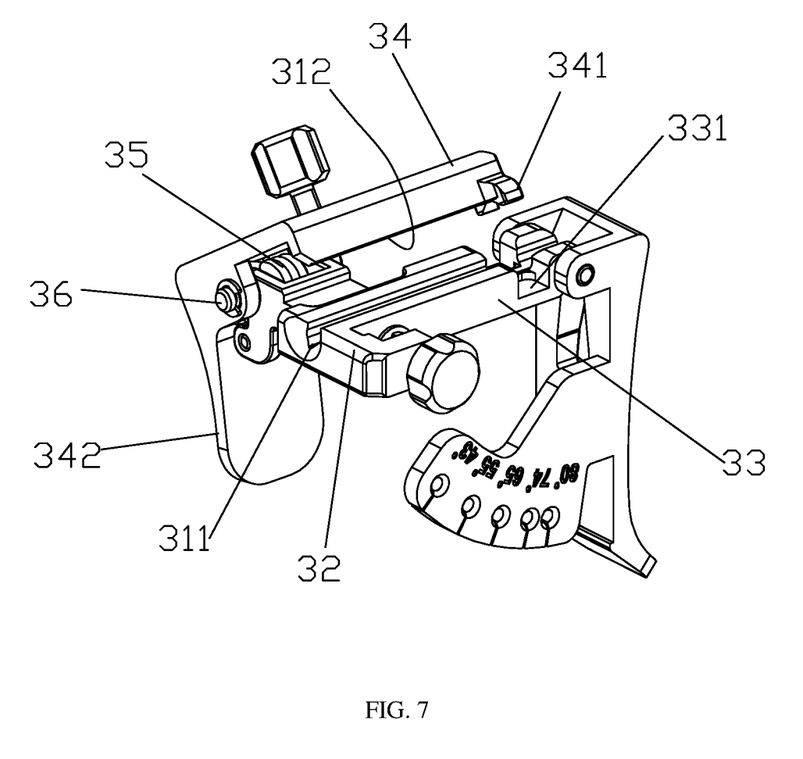
FIG. 7 is a schematic structural diagram of a needle guiding base according to an embodiment of the present application.

FIG. 7 further shows the specific structure of the needle guiding base 30 according to an embodiment of the present application. As shown in FIG. 7, the needle guiding base 30 comprises a first guiding seat 33 and a second guiding seat 34. The first guiding seat 33 is rotatably connected with the angle fixing base 20 at their first ends through the rotating shaft 40, and the aforementioned U-shaped limiting assembly 32 is formed at a second end of the first guiding seat 33. The first guiding seat 33 is provided with a needle guiding channel 311 penetrating from the first end to the second end. The second guiding seat 34 is disposed relative to the first guiding seat 33, and the second guiding seat 34 has a matching surface 312 penetrating from the first end to the second end. The first guiding seat 33 and the second guiding seat 34 are rotatably connected on opposite sides through a shaft 36, and at least an elastic member 35 is further provided between the first guiding seat 33 and the second guiding seat 34. Elastic force of the elastic member 35 causes the matching surface 312 on the second guiding seat 34 to move toward the needle guiding channel 311 on the first guiding seat 33, so that the matching surface 312 and the needle guiding channel 311 together form the needle tract 31 for guiding the biopsy needle. Specifically, as shown in FIG. 7, the elastic member 35 is a torsion spring installed on the shaft 36, with one end of the torsion spring being abutted against the first guiding seat 33, and the other end being abutted against the second guiding seat 34. The elastic force of the torsion spring acts on the first guiding seat 33 and on the second guiding seat 34, causing the matching surface 312 of the second guiding seat 34 always has a tendency to move close to the needle guiding channel 311 of the first guiding seat 33.

Further as shown in FIG. 7, at least one groove 331 traversing the needle guiding channel 311 is provided on the first guiding seat 33 from the first end to the second end corresponding to the needle guiding channel 311. On the other hand, two engaging members 341 extends respectively from two sides on the matching surface 312 of the second guiding seat 34 at a position corresponding to the grooves 331. Under the action of the elastic force of the elastic member 35, the engaging members 341 also always have a tendency to move into the corresponding groove 331. Cooperation of the engaging members 341 and the groove 331 brings a larger free movement space by the biopsy needle overcoming the pressure of the elastic member 35 during the operation, which facilitates the biopsy needle swinging to adjust its position in this free movement space and is beneficial to needle insertion. Moreover, the engaging members 341 protrude from both sides of the matching surface 312, and can quickly pull the biopsy needle back into the needle guiding channel 311 under the action of the elastic member 35 to prevent the whole biopsy needle from slipping out of the needle guiding channel 311.

Further as shown in FIG. 7, there is an operating end 342 on the second guiding seat 34. The operating end 342 extends out from the second guiding seat 34 at one side of the shaft 36 that is away from the needle guiding channel 311. By pressing the operation end 342, the second guiding seat 34 is rotated relative to the first guiding seat 33 against the elastic force of the elastic member 35 to open the needle tract 31. It is convenient for the needle guiding base 30 to clean the needle tract 31 by means of the second guiding seat 34 being rotatable and openable relative to the first guiding seat 33.

The above is only the preferred embodiments of the present application, and is not intended to limit the present application. Any modifications, equivalent substitutions and improvements made within the spirit and principles of the present application should be included within the protection scope of the present application.

What is claimed is:

1. A device for adjusting biopsy angles, comprising an angle fixing base and a needle guiding base, the needle guiding base being rotatably connected with the angle fixing base at their first ends, and the needle guiding base having a needle tract for guiding a biopsy needle, characterized in that:
   an angle fixing sheet extends from a second end of the angle fixing base, and two or more positioning holes are distributed on the angle fixing sheet with a certain radius around a rotation axis at the first ends of the needle guiding base and the angle fixing base, and opening slots corresponding to and penetrating to each of the positioning holes are formed on an outer edge of the angle fixing sheet;
   a U-shaped limiting assembly is formed at a second end of the needle guiding base on the side opposite to the angle fixing sheet, wherein the U-shaped limiting assembly is formed by an enclosure of a first limiting plate extending laterally from one side of the second end of the needle guiding base, a second limiting plate extending vertically from the first limiting plate and the needle guiding base, and an outer side surface of the needle guiding base and an inner side surface of the second limiting plate serve as an inner side limiting surface and an outer side limiting surface of the U-shaped limiting assembly respectively, and the U-shaped limiting assembly surrounds the angle fixing sheet therein, and at least an inner side surface of the angle fixing sheet is in contact with the inner side limiting surface of the U-shaped limiting assembly; and
   the device for adjusting biopsy angles further comprises a positioning post which movably penetrates through the second limiting plate and is movably engaged with the positioning holes on the angle fixing sheet so as to be inserted into the positioning holes or be released out of the positioning holes.

2. The device for adjusting biopsy angles according to claim 1, wherein the positioning post penetrates through the second limiting plate by means of elastically loaded shaft-hole cooperation or threaded rotation, and the positioning post has an operating portion at its outer end.

3. The device for adjusting biopsy angles according to claim 1, wherein the positioning hole is formed with a tapered groove, and a tapered platform corresponding to the tapered groove is provided at an inner end of the positioning post.

4. The device for adjusting biopsy angles according to claim 1, wherein a retaining ring is provided at an inner end of the positioning post passing through the second limiting plate, and when the retaining ring abuts against the inner side surfaces of the second limiting plate, the positioning post is prevented from being disengaged from the second limiting plate.

5. The device for adjusting biopsy angles according to claim 1, wherein the needle guiding base is rotatably connected with the angle fixing base at their first ends through a rotating shaft.

6. The device for adjusting biopsy angles according to claim 1, wherein the needle guiding base further comprises:
   a first guiding seat, the first guiding seat having a needle guiding channel penetrating from the first end to the second end and at least one groove traversing the needle guiding channel provided from the first end to the second end corresponding to the needle guiding channel;
   a second guiding seat, the second guiding seat having a matching surface that cooperates with the needle guiding channel and engaging members that extends respectively from two sides on the matching surface at a position corresponding to the groove; and
   the second guiding seat is rotatably mounted on the first guiding seat by means of elastic loading configuration, and elastic force of the elastic loading configuration causes the matching surface on the second guiding seat to have a tendency to move close to the needle guiding channel of the first guiding seat, so that the matching surface and the needle guiding channel together form the needle tract; and the elastic force of the elastic loading configuration also causes the engaging members on the second guiding seat to have a tendency to move into the corresponding groove on the first guiding seat, so that the engaging members are positioned in the corresponding groove;
   wherein the first end of the first guiding seat is rotatably connected with the angle fixing base, and the U-shaped limiting assembly is formed at the second end of the first guiding seat.

7. A biopsy needle guide, comprising a mounting assembly used for cooperating with an ultrasound probe, characterized in that, further comprising a device for adjusting biopsy angles which comprises an angle fixing base and a needle guiding base, the angle fixing base being arranged on the mounting assembly, the needle guiding base being rotatably connected with the angle fixing base at their first ends, and the needle guiding base having a needle tract for guiding a biopsy needle, wherein:
   an angle fixing sheet extends from a second end of the angle fixing base, and two or more positioning holes are distributed on the angle fixing sheet with a certain radius around a rotation axis at the first ends of the needle guiding base and the angle fixing base, and opening slots corresponding to and penetrating to each of the positioning holes are formed on an outer edge of the angle fixing sheet;

a U-shaped limiting assembly is formed at a second end of the needle guiding base on the side opposite to the angle fixing sheet, wherein the U-shaped limiting assembly is formed by an enclosure of a first limiting plate extending laterally from one side of the second end of the needle guiding base, a second limiting plate extending vertically from the first limiting plate and the needle guiding base, and an outer side surface of the needle guiding base and an inner side surface of the second limiting plate serve as an inner side limiting surface and an outer side limiting surface of the U-shaped limiting assembly respectively, and the U-shaped limiting assembly surrounds the angle fixing sheet therein, and at least an inner side surface of the angle fixing sheet is in contact with the inner side limiting surface of the U-shaped fixing limiting assembly; and the device for adjusting biopsy angles further comprises a positioning post which movably penetrates through the second limiting plate and is movably engaged with the positioning holes on the angle fixing sheet so as to be inserted into the positioning holes or be released out of the positioning holes.

8. The biopsy needle guide according to claim 7, wherein the positioning post penetrates through the second limiting plate by means of elastically loaded shaft-hole cooperation or threaded rotation, and the positioning post has an operating portion at its outer end.

9. The biopsy needle guide according to claim 7, wherein the positioning hole is formed with a tapered groove, and a tapered platform corresponding to the tapered groove is provided at an inner end of the positioning post.

10. The biopsy needle guide according to claim 7, wherein a retaining ring is provided at an inner end of the positioning post passing through the second limiting plate, and when the retaining ring abuts against the inner side surfaces of the second limiting plate, the positioning post is prevented from being disengaged from the second limiting plate.

11. The biopsy needle guide according to claim 7, wherein the needle guiding base is rotatably connected with the angle fixing base at their first ends through a rotating shaft.

12. The biopsy needle guide according to claim 7, wherein the needle guiding base further comprises:

a first guiding seat, the first guiding seat having a needle guiding channel penetrating from the first end to the second end and at least one groove traversing the needle guiding channel provided from the first end to the second end corresponding to the needle guiding channel;

a second guiding seat, the second guiding seat having a matching surface that cooperates with the needle guiding channel and engaging members that extends respectively from two sides on the matching surface at a position corresponding to the groove; and the second guiding seat is rotatably mounted on the first guiding seat by means of elastic loading configuration, and elastic force of the elastic loading configuration causes the matching surface on the second guiding seat to have a tendency to move close to the needle guiding channel of the first guiding seat, so that the matching surface and the needle guiding channel together form the needle tract; and the elastic force of the elastic loading configuration also causes the engaging members on the second guiding seat to have a tendency to move into the corresponding groove on the first guiding seat, so that the engaging members are positioned in the corresponding groove;

wherein the first end of the first guiding seat is rotatably connected with the angle fixing base, and the U-shaped limiting assembly is formed at the second end of the first guiding seat.

* * * * *